United States Patent [19]
Coles

[11] Patent Number: 5,722,967
[45] Date of Patent: Mar. 3, 1998

[54] SANITARY NAPKIN HAVING SHAPING MEANS

[75] Inventor: Peter Coles, Kelkheim Fischbach, Germany

[73] Assignee: The Procter & Gamble Company, Cincinnati, Ohio

[21] Appl. No.: 759,292

[22] PCT Filed: Sep. 20, 1993

[86] PCT No.: PCT/US93/08848

§ 371 Date: Mar. 20, 1995

§ 102(e) Date: Mar. 20, 1995

[87] PCT Pub. No.: WO94/06386

PCT Pub. Date: Mar. 31, 1994

Related U.S. Application Data

[63] Continuation of Ser. No. 403,896, Mar. 20, 1995, abandoned.

[30] Foreign Application Priority Data

Sep. 21, 1992 [EP] European Pat. Off. ............ 92308588

[51] Int. Cl.⁶ ............................ A61F 13/15; A61F 13/20
[52] U.S. Cl. .................... 604/385.1; 604/378; 604/387
[58] Field of Search ............................ 604/367, 368, 604/369, 374, 378, 379, 380, 387, 385, 400

[56] References Cited

U.S. PATENT DOCUMENTS

| | | |
|---|---|---|
| 4,758,240 | 7/1988 | Glassman ............... 604/379 |
| 4,950,264 | 8/1990 | Osborn, III. |
| 5,069,676 | 12/1991 | Ito et al. ............... 604/380 |
| 5,074,856 | 12/1991 | Coe et al. ............ 604/385.1 |
| 5,171,302 | 12/1992 | Buell. |
| 5,181,563 | 1/1993 | Amaral ............... 604/385.1 |
| 5,197,959 | 3/1993 | Buell. |
| 5,300,055 | 4/1994 | Buell. |
| 5,312,386 | 5/1994 | Correa et al. ........ 604/385.1 |
| 5,318,553 | 6/1994 | Weeks et al. ........ 604/385.1 |
| 5,324,278 | 6/1994 | Visscher et al. ..... 604/385.1 |
| 5,451,442 | 9/1995 | Pieniak et al. ........ 604/379 |
| 5,460,623 | 10/1995 | Emenaker et al.. |

FOREIGN PATENT DOCUMENTS

| | | |
|---|---|---|
| A-32360/84 | 8/1984 | Australia. |
| B-49757/90 | 8/1990 | Australia. |
| B-65103/90 | 4/1991 | Australia. |
| 9416658 | 8/1994 | WIPO ............... 604/380 |

*Primary Examiner*—John G. Weiss
*Assistant Examiner*—Ki Yong O
*Attorney, Agent, or Firm*—Theodore P. Cummings; Steven W. Miller; Jacobus C. Rasser

[57] ABSTRACT

In a sanitary napkin, longitudinal score lines applied to the core and longitudinal glue lines located adjacent to the score lines, cause controlled deformation of the sanitary napkin's absorbent core upon lateral compression and provide increased resiliency for the sanitary napkin to return to its undeformed state when the compressive forces are removed.

1 Claim, 3 Drawing Sheets

SANITARY NAPKIN HAVING SHAPING MEANS

This is a continuation of application Ser. No. 08/403,896, filed on Mar. 20, 1995, now abandoned.

FIELD OF THE INVENTION

The invention relates to sanitary napkin comprising a liquid pervious topsheet, a liquid impervious backsheet and an absorbent core comprised between the topsheet and the backsheet, the absorbent core having a garment facing surface, a body facing surface, a longitudinal center line and two longitudinal sides generally parallel to the longitudinal center line, the absorbent core comprising shaping means for raising a central part of the core's body facing surface upon compression of the core transverse to the longitudinal sides.

Such a sanitary napkin is known from EP Patent No. 0 335 252. In this patent application a sanitary napkin is described that has a flexure resistant deformation element that can be placed at the position of the backsheet. Upon deformation of the element by compression by the user's thighs, the flexure resistant element causes the core to adopt a generally W-shaped configuration. This causes a good contact between the topsheet of the sanitary napkin, a central pan of which is pushed upward, and the body of the wearer during use.

It is an object of the invention to provide a sanitary napkin conforming closely to the body of the wearer during use and being comfortable.

It is another object of the invention to provide a sanitary napkin in which undesirable bunching during use is reduced.

It is again another object of the invention to provide a sanitary napkin comprising shaping means of relatively simple nature, giving a well-defined deformation of the absorbent core during use.

It is another object of the invention to provide a sanitary napkin that relaxes to a generally flattened state when pressure exerted by the user's thighs on the sanitary napkin is reduced.

SUMMARY OF THE INVENTION

A sanitary napkin according to the invention is characterized in that the shaping means comprise two axes of flexibility of the core, one axis of flexibility extending on each side of the longitudinal center line and generally parallel thereto, the stiffness of the core being reduced along each axis of flexibility, each axis of flexibility forming an axis of inflexion of the core's body facing side upon compression of the core transverse to the core's longitudinal sides.

By reducing the stiffness of the core along the axes of flexibility, for instance by scoring, embossing, perforating or cutting the core along these axes, the central area of the core located between the axes of flexibility will rise upward upon compression of the core in a direction transverse to the longitudinal center line. The deformation of the core is controlled by the axes of flexibility so that undesired bunching and formation of longitudinal channels, along which liquids can be transported to the perimeter of the sanitary napkin, are reduced.

Providing the core with axes of flexibility causes the central part of the core and the topsheet to remain close to the loading point for efficient acquisition of liquids discharged from the user's vestibule, while the areas flanking the central region remain relatively flat for providing a maximum coverage of the undergarment.

The axes of flexibility also reduce the forces necessary for initial deformation (before the napkin is wetted) and hence increase the comfort of the sanitary napkin for the wearer.

In an embodiment of an absorbent article according to the invention, the core comprising an absorption layer and a fluid handling layer located between the absorption layer and the topsheet is characterized in that the shaping means comprise a pair of bond lines, one bond line extending on either side of the longitudinal center line near the axes of flexibility, generally parallel thereto, or coincident with the axes of flexibility, the absorption layer and the fluid handling layer being bonded along the bond lines.

The absorbent core can comprise a number of layers, such as for instance a "laminate" of two fibrous layers between which an absorbent gelling material is comprised, and a wipe acquisition sheet overlying the laminate for lateral distribution of the liquid across the laminate's surface. Such a core is described in U.S. Pat. No. 4,950,264.

Joining together of the laminate and the wipe acquisition sheet near the axes of flexibility, couples the deformation of the layers in the core, so that the well defined deformation of the lower layer is transmitted to the upper layer. The bonding of the layers can occur for instance by embossing only, so that the bond lines at the same time form the axes of flexibility. Other means of bonding are fusion bonding under application of heat and pressure or ultrasonic fusion bonding. Preferably the layers are bonded by an adhesive in such a way that the liquid-handling properties of the layers are not substantially affected.

Upon removal of the compressive forces exerted on the sanitary napkin during use, the elastic forces in the central parts of each layer that has been raised, collectively act upon the bond lines to flatten the sanitary napkin. This results in a increased resiliency of the sanitary napkin and consequently of a better coverage of the undergarment.

Preferably the adhesive of the bond lines is applied in a spiral pattern, which has a relatively low depth of penetration into the layer onto which the spiral glue pattern is applied.

In an embodiment of a sanitary napkin according to the invention, the bond lines extend along between 25% and 100% of the length of the absorbent core, preferably along 30% and 85%, the width of each bond line being between 2 and 16 mm, preferably between 3 and 9 mm, the amount of adhesive in each line being between 0.001 and 0.03 grams, preferably between 0.02 and 0.029 grams, the distance of the bond lines from the longitudinal center line being between 7 and 23 mm, preferably between 10 and 20 mm, a spacing between two adjacent loops in each spiral being between 1 and 10 mm, preferably between 3 and 7 mm, the number of bond lines being between 2 and 8, preferably between 2 and 4.

In another embodiment of an absorbent article according to the invention, the absorbent core is at its garment facing surface connected to the backsheet, the backsheet being on its garment-facing side provided with a layer of adhesive, the adhesive not extending along the area of the backsheet located between a projection of the axes of flexibility onto the backsheet.

Bonding of the core to the backsheet prevents shifting of the core within the space between the topsheet and the backsheet. Preferably the garment facing side of the backsheet is glued to the inside of the garment using a pressure sensitive adhesive to keep the sanitary napkin in place during use. When the sanitary napkin is compressed during use, the backsheet is raised, together with the central pan of the core. It is essential that the part of the backsheet that is raised together with the core, is not glued to the garment, so that it does not impair the deformation of the core.

Again another embodiment of an absorbent article according to the invention is characterized in that the core comprises a central acquisition zone comprising a lower amount of absorbent gelling material than the zones of the core surrounding the acquisition zone.

The omission of absorbent gelling material in the central zone of the sanitary napkin according to the invention, results in a better longitudinal distribution of liquids in the absorbent core and in faster acquisition. A sanitary napkin having a central acquisition zone of reduced concentration of absorbent gelling material is known from European patent application number: 92306824.1 filed on Jul. 27, 1992 in the name of The Procter & Gamble Company. The reduction of absorbent gelling material in the central zone, reduces the stiffness of the central zone relative to the zones of the core that surround the central zone. This facilitates the deformation of the central pan of the core upon compression of the core transverse to the longitudinal sides. The central zone of the core can be given an embossment for imparting further flexibility.

BRIEF DESCRIPTION OF THE DRAWINGS

Some embodiments of a sanitary napkin according to the invention will be described with reference to the accompanying drawings. In the drawings.

DETAILED DESCRIPTION OF THE INVENTION

Figures 1, 2:
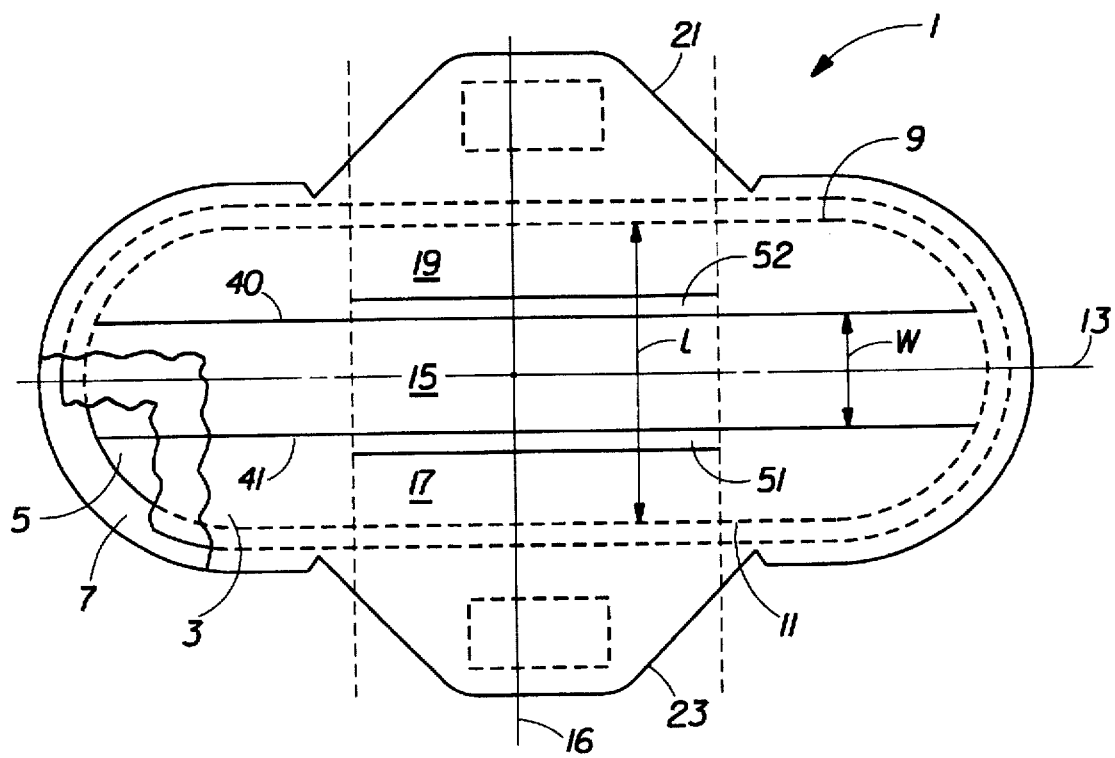
FIG. 1 shows a top plan view of a sanitary napkin wherein a part of the overlying layers have been cut away to expose underlying structures, the sanitary napkin having a generally straight core.
FIG. 2 shows a top plan view of a sanitary napkin having a shaped core.

The embodiments of the absorbent article as illustrated in the drawings refer to a disposable sanitary napkin, i.e. an article which is worn by females adjacent to the pudendal region and which is intended to absorb and contain the various exudates which are discharged from the body (e.g. blood, menses and urine) and which are intended to be discarded after a single use. The invention is however not limited to sanitary napkins only, but also covers other absorbent articles such as pantiliners, which generally have a lower capacity than sanitary napkins. Although the embodiment described in detail in the drawings has a so called "laminate" core wherein the absorbent gelling material is present as a layer between two sheets, the invention is not limited thereto and also applies to Cores wherein the absorbent gelling material is mixed with fibers, such as described in the American patent application No. 07/810, 774, filed on Dec. 17, 1991 in the name of The Procter & Gamble Company, which is hereby incorporated by reference.

FIG. 1 shows a sanitary napkin 1 comprising a liquid pervious topsheet 3, an absorbent core 5 underlying the topsheet and a liquid impervious backsheet 7. The core 5 has two longitudinal sides 9 and 11, which extend in a generally longitudinal direction of a longitudinal center line 13 of the core 5. The longitudinal sides 9,11 need not be straight but can also be curved towards the longitudinal center line, to provide a shaped core, as shown in FIG. 2. The absorbent core 5 can be covered by one or more acquisition layers for distributing fluids which have penetrated through the topsheet 3, across the absorbent core 5. The absorbent core 5 comprises a laminate wherein the absorbent gelling material is interposed between an upper tissue 24 and a lower tissue 25.

Figure 6A:
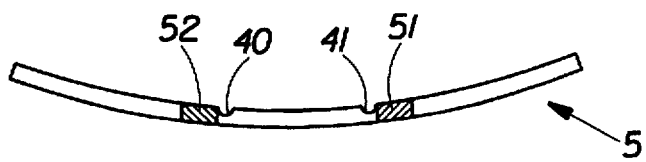
FIG. 6a and 6b show a schematic cross sectional view of a sanitary napkin according to the invention before and after compression thereof.
Figure 6B:
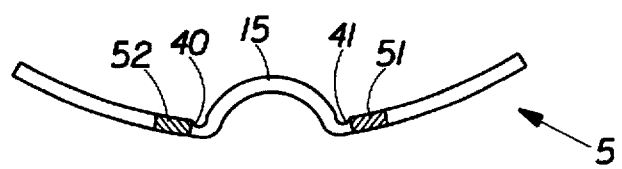

Parallel to the core's longitudinal center line 13 extend a pair of axes of flexibility 40 and 41, along which the core 5 has a reduced resistance against compression forces acting transverse to the longitudinal sides 9, 11. The preferred axes of flexibility as shown in FIGS. 1 and 2 are straight, but can be of inwardly concave or convex shape; Upon compression of the core transverse to the longitudinal sides 9, 11, the central part 15 of core that is located between the axes of flexibility 40, 41, that are preferably formed by scoring of the core, will raise in an upward direction so as to remain in close contact with the user's body. This is schematically illustrated in FIGS. 6a and 6b.

In a preferred embodiment, the core 5 comprises at least two layers, that are bonded together along bond lines 51, 52 located adjacent to axes of flexibility 40, 41. Bonding of the layers of the core along the bond lines 51, 52 imparts an increased flexibility to the core 5 making it return to its undeformed shape when compression forces on the core are removed.

The core 5 can be provided with a central acquisition zone 18 that is flanked by two side zones 17 and 19. The central acquisition zone 18 comprises a lower concentration of absorbent gelling materials than the side zones, the concentration in the side zones 17,19 being between 2 and 7.5 g./sq. foot, preferably about 5.5 g/sq foot, for a relatively low gel strength absorbent gelling material and between 2 and 15 g/sq foot, preferably about 10 g/sq foot for relatively high gel strength absorbing gelling materials, and in the acquisition zone being preferably about 0 g/sq. foot. A test method for measuring the gel strength is described in European Patent application No. 92201394.1, filed on May 15, 1992 in the name of The Procter & Gamble Company which is hereby incorporated by reference.

The concentration of absorbent gelling material need not change abruptly when going from the side zones to the acquisition zone, but can for instance decrease linearly from high to low, or according to any other desired profile.

The width, W, of the central part 15 of the core 5 preferably is narrow compared to the narrowest width, L, of the absorbent core 5. Preferably the distance W between the score lines corresponds to the width of the central acquisition zone 18 of reduced concentration of absorbent gelling material, which in a preferred embodiment amounts to 3 turn. For sanitary napkins having a shaped core 5, as is shown in FIG. 2, the narrowest lateral dimension L of the sanitary napkin is located along the transverse center line 16 thereof and measures preferably about 70 mm. The sanitary napkin I is at its longitudinal perimeter provided with two lateral flaps or wings, which can during use be folded around the edge of the user's garment to position the sanitary napkin width respect to the garment and to reduce side soiling.

Looking at some of the elements of the sanitary napkin more specifically, the absorbent core 5 may be any means which is generally compressible, conformable, non-irritating to the wearer's skin and capable of absorbing and containing body exudates. The absorbent core 5 may be manufactured in a wide variety of sizes and shapes (e.g. rectangular, hour-glass, etc.). A preferred shape of the absorbent core 5 is the dogbone shape shown in FIG. 2. This preferred absorbent core 5 is about 22.0 centimeters long (longitudinal dimension along the longitudinal centerline 13), about 7.0 centimeters wide across its midportion (lateral dimension) along the traverse center line 16. The absorbent core 5 is symmetrically configured for ease of manufacture and so that no conscious effort is required by the wearer to properly place the napkin 1 in the direction it should be worn. The midportion is configured to basically conform to the wearer's thighs and to the thinner crotch portion of the wearer's panties so as to prevent excessive bunching. The size of the absorbent core 5 may be varied to accommodate wearers ranging in size and also ranging in the expected amount of exudate fluid volume. The absorbent core 5 may be attached over the core's major top and bottom surfaces respectively, to adjacent members such as the topsheet 3 and back sheet 7 by any of the means well known in the art, such as by spray-gluing lines or spots of adhesive. Such attachment facilitates integrity and recoverability of the absorbent materials in use so as to maintain an optimum degree of absorbency. Preferably, the absorbent core 5 has a wet-tensile strength in the cross-direction of at least about 100.0 grams per centimeter. Wet tensile strength is determinable by ASTM Standard D 829-49.

The absorbent core 5 may be manufactured from a wide variety of liquid absorbent materials commonly used in disposable sanitary napkins, diapers, and other absorbent articles. Examples of suitable absorbent materials include comminuted wood pulp which is generally referred to as airfelt, creped cellulose wadding, absorbent foam, absorbent sponges, synthetic staple fibers, polymeric fibers, hydrogel-forming polymer gelling agents, or any equivalent materials or combinations of materials. A particularly preferred absorbent material are absorbent gelling materials or polymeric gelling agents. Polymeric gelling agents are those materials which, upon contact with fluids (i.e., liquids) such as water or body fluids, imbibe such fluids and thereby form hydrogels. In this manner, fluid discharged into the absorbent core 5 can be acquired and held by the polymeric gelling agent, thereby providing the articles herein with enhanced absorbent capacity and/or improved fluid retention performance.

The polymeric gelling agent which is employed in the absorbent core 5 will generally comprise particles of a substantially water-insoluble, slightly cross-lined, partially neutralized, hydrogel-forming polymer material. Such polymer materials can be prepared from polymerizable, unsaturated, acid-containing monomers. Suitable unsaturated acidic monomers for use in preparing the, polymeric gelling agents used in this invention include those listed in U.S. Pat. No. 4,654,039, entitled "Hydrogel-Forming Polymer Compositions for Use in Absorbent Structures", which issued to Brandt, Goldman and Inglin on Mar. 31, 1987, and which patent is incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agent the polymeric component formed from unsaturated, acid-containing monomers my be grafted onto other types of polymer moieties such as starch or cellulose. Polyacrylate grafted starch materials of this type are especially preferred for use herein.

Preferred polymer gelling agents which can be prepared from conventional types of monomers include hydrolyzed acrylonitrile grafted starch, polyacrylate grafted starch, polyacrylates; maleic anhydride-based copolymers and combinations thereof. Especially preferred are the polyacrylates and polyacrylate grafted starch.

Whatever the nature of the basic polymer components of the hydrogel-forming polymeric gelling agents used in the absorbent core 5 herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in U.S. Pat. No. 4,076,663, which patent issued to Masuda et al on Feb. 28, 1978, and which patent is incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5.0 mole percent of the resulting hydrogel-forming polymer material. More preferably, the cross-linking agent will comprise from about 0.01 mole percent to 3.0 mole percent of the hydrogel-forming polymeric gelling agent used herein.

The slightly cross-linked, hydrogel-forming polymeric gelling agents which may be used in the articles of the present invention are generally employed in their partially neutralized form. For purposes of this invention, such materials are considered partially neutralized when at least 25.0 mole percent and preferably at least 50.0 mole percent of monomers used to form the polymer are acid group-containing monomers which have been neutralized with a salt-forming cation. Suitable salt-forming cations include alkali metal, ammonium, substituted ammonium, and amines. This percentage of the total monomer utilized which are neutralized acid group-containing monomers is referred to herein as the "degree of neutralization".

The polymeric gelling agent materials used in the absorbent articles as shown in FIGS. 1 to 4 must have a relatively high capacity for imbibing fluids encountered in such articles. The absorbent capacity of these materials can be quantified by referencing the "gel volume" of the polymeric gelling agents which are to be selected for use in the present invention.

For purposes of this invention, gel volume can be defined in terms of the amount of synthetic urine absorbed by any given polymeric gelling agent and is specified as grams of synthetic urine per gram of polymeric gelling agent. Gel volume in synthetic urine can be determined for forming a suspension of about 0.1–0.2 parts of dried polymeric gelling agent to be tested with about 20 parts of synthetic urine. This suspension is maintained at ambient temperature under gentle stirring for a time sufficient, e.g., about 1 hour, for swelling equilibrium to be attained. The gel volume of the polymeric gelling agent is then calculated from the weight fraction of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension.

The gel volume of the gelling agents used in the absorbent core 5 herein will generally be at least about 20.0 grams of synthetic urine per gram of polymeric gelling agent. More preferably, the gel volume of the materials employed will range from about 20.0 to about 60.0, most preferably from about 22.0 to about 35.0 grams of synthetic urine per gram of polymeric gelling agent.

The absorbent gelling materials having an absorbent gel strength of more that 1.2 kPa after 5 minutes are classified as high gel strength absorbent gelling materials and can be used in higher concentrations in the side zones. Preferred absorbent gelling materials show a generally regular increase in gel strength from the value after 5 minutes exposure to the value after 30 minutes exposure.

In the preferred embodiments shown in FIGS. 3–8, the absorbent core 5 is a laminate comprised of a layer of absorbent gelling material disposed between two air-laid tissues 24 and 25. A suitable laminate is the WATER-LOCK L-535® absorbent laminate available from the Grain Processing Corporation of Muscatin, Iowa. Such superabsorbent laminates are disclosed in U.S. Pat. No. 4,467,012, entitled "Composition for Absorbent Film and Method of Preparation", which patent issued to Pedersen et al. on Aug. 21, 1984, and U.S. Pat. No. 4,260,443, entitled "Laminated Absorbent Process", which patent issued to Lindsay et at. on Apr. 7, 1981, and which patents are incorporated herein by reference. The WATER-LOCK L-535® absorbent laminate has a hydrogel polymer loading of 0.005 grams per square centimeter, however, loadings of 0.001–0.009 grams per square centimeter have been found acceptable. The first and second tissue layers 24 and 25 provide containment of the absorbent polymer material, improve lateral wicking of the absorbed exudates throughout the absorbent core 5 and provide a degree of absorbency. In the case of non-particulate hydrogel-forming polymer gelling agents which can be formed into fibrous sheets, foams or films, the non-particulate gelling agent may comprise from about 15% to about 100% by weight of the absorbent core 5, more preferably of from about 40% to about 100%, and most preferably of from about 60% to about 100%. Two suitable and commercially available non-particulate absorbent materials of relatively low gel strength for use in the absorbent core 5 are a double layer acrylic fibrous material available under the tradename Lanseal F from the Choli Company, LTD., of Higashi, Osaka, Japan and a carboxymethylcellulose fibrous material available under the tradename Aqualon C from Hercules, Inc. of Wilmington, Del.

The total absorbent capacity of the absorbent core 5 should be compatible with the design exudate loading for the intended use of the sanitary napkin 1. Further, the absorbent capacity of the absorbent core 5 may be varied to accommodate wearers ranging in the expected amount of exudate fluid volume. For instance, a different absorbent capacity may be utilized for sanitary napkins intended for daytime use as compared with those intended for night-time use, or for sanitary napkins intended for use by teenage females as compared with those intended for use by more mature women.

Figure 3:
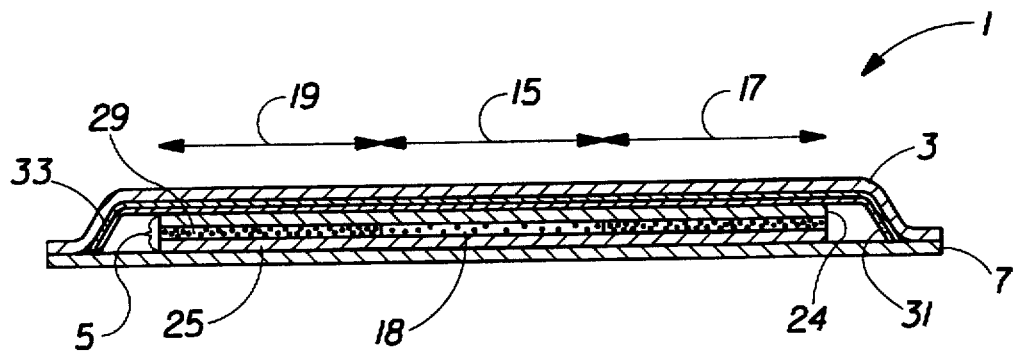
FIG. 3 shows a cross sectional view of the sanitary napkin of FIG. 1 along the transverse center line 16.

Superimposed over the absorbent core 5 and extending 3.0 millimeters beyond the edges 9 and 11 of the absorbent core 5 can be placed wet-laid tissue 31 as shown in FIG. 3. The wet-laid tissue 31 is liquid permeable. A satisfactory wet-laid tissue 31 has a basic weight of about 15.8 grams per square meter and an air permeability of about 30.5 cubic meters per minute per square meter at a pressure differential of about 12.08 millimeters of water.

Preferably, the wet-laid tissue 31 maintains integrity when wetted, in use. The wet-laid tissue 31 preferably has a wet tensile strength in the cross-direction of at least about 15.0 grams per centimeter. Suitable tissues 31 and their manufacture are disclosed in U.S. Pat. No. 3,301,746, entitled "Process for Forming Absorbent Paper by Imprinting a Fabric Knuckle Pattern thereon prior to Drying and Paper thereof", which patent issued to Sanford and Sisson on Jan. 31, 1967, and which patent is incorporated herein by reference. In a preferred embodiment, those parts of the wet-laid tissue 31 which extend beyond the longitudinal sides 9 and 11 of the absorbent core 5 are associated with the back sheet 7. The wet-laid tissue 31 may be associated with the back sheet 7 by attachment means as are well known in the art such as by spray-gluing on lines or spots of adhesive. The wet-laid tissue 31 serves a number of purposes. The tissue 31 serves to confine any loose superabsorbent material 29 between the tissue 31 and the back sheet 7 thereby preventing the superabsorbent material 29 from coming in contact with the wearer's skin. Also, the tissue 31 improves lateral wicking of the absorbed exudates over the absorbent core 5 thereby providing a more even distribution of the exudates throughout the absorbent core 5. Further, the tissue 31 provides some degree of absorbency and further inhibits exudates which have reached and been absorbed by the absorbent core 5 from rewetting the wearer's skin.

Superimposed over the wet-laid tissue 31 can be a liquid permeable wipe acquisition sheet 33. In a preferred embodiment, the wipe acquisition sheet 33 is a nonwoven sheet, such as a spunlaced 70%/30% rayon/polyester fiber sheet. Spunlaced fabrics of this type are manufactured by E.I. DuPont Nemours and Company of Wimington, Del., and are made available under the SONTARA® spunlaced fibers. These fabrics are available in a number of suitable styles, however, Style 8407 in its apertured form, having a basis weight of 0.005 grams per square centimeter and a thickness of about 0.04 millimeters, is preferred. The wipe acquisition sheet 33 extends beyond the edges of the wet-laid tissue 31 where it too is associated with back sheet 7. The wipe acquisition sheet 33 greatly improves lateral wicking of exudates over the absorbent core 5 thereby, in combination with the central acquisition zone 15, providing a more even distribution of the exudates throughout the absorbent core 5. The lateral wicking of the wipe acquisition sheet 33, in combination with the longitudinal spread of liquids in the central acquisition zone 15, is important for the following reason. Many bulky prior art sanitary napkins rely on a high degree of vertical absorption at the point where exudates are initially deposited. In other words, because the absorbent cores of these napkins are fairly thick, they can absorb a high degree of exudates throughout their thickness while utilizing only a small degree of their surface area or lateral absorption capability.

However, the relatively thin napkins 10 of the present invention have a comparatively small degree of vertical absorption. Therefore, for a relatively large amount of exudates to be absorbed, a wipe acquisition sheet 33, and a central acquisition zone 15, which can transversely and longitudinally, disperse the exudates over a large surface area of the absorbent core 5 where the exudates can better and faster be vertically absorbed is highly desirable.

Superimposed over the wipe acquisition sheet 33 is the liquid permeable topsheet 3. In a preferred embodiment, the topsheet 3 is associated with the wipe acquisition sheet 33 by spray-gluing the topsheet 3 to the surface of the wipe acquisition sheet 33. The topsheet 3 is compliant, soft feeling, and non-irritating to the wearer's skin. Further, the topsheet 3 is liquid pervious, permitting liquid to readily transfer through its thickness. A suitable topsheet 3 may be manufactured from a wide range of materials such as polymeric materials, formed thermoplastic films, apertured plastic films, porous foams, reticulated foams, natural fibers (e.g., wood or cotton fibers), synthetic fibers, (e.g., polyester or polypropylene fibers) or from a combination of natural and synthetic fibers, with apertured formed films being preferred. Formed films are preferred for the topsheet 3 because they are pervious to liquids and yet non-absorbent. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structure having Tapered Capillaries", which patent issued to Thompson on Dec. 30, 1975, U.S. Pat. No. 4,324,246, entitled "Disposable Absorbent Article having a Stain Resistant Topsheet", which patent issued to Mullane and Smith on Apr. 13, 1982, U.S. Pat. No. 4,342, 314, entitled "Resilient Plastic Web Exhibiting Fiber-like Properties", which paint issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-like Tactile Impression", which patent issued to Ahr. Louis, Mullane, and Ouellette on Jul. 31, 1984, all of which patents are incorporated herein by reference.

In a preferred embodiment of the present invention, the body surface of the topsheet 3 is hydrophilic. The hydrophilic body surface helps liquid to transfer through the topsheet 3 faster than if the body surface was not hydrophilic. This diminishes the likelihood that menstrual fluid will flow off the topsheet 3 rather than being absorbed by the absorbent core 5. In a preferred embodiment, the body surface of the topsheet 3 is made hydrophilic by treating the body surface with a surfactant. It is preferred that the surfactant be substantially evenly and completely distributed throughout the body surface of the topsheet 3. This can be accomplished by any of the common techniques well know to those skilled in the art. For example, the surfactant can be applied to the topsheet 3 by spraying, by padding, or by the use of transfer rolls. Further, the surfactant can be incorporated into the polymeric materials of a formed film topsheet or between or within the fibers of a nonwoven topsheet.

The back sheet 7 is adjacent the absorbent core 5. In a preferred embodiment, the absorbent core may be affixed to the back sheet 7. Any of the common techniques well known in the art, such as spray-gluing or lines or spots of adhesive may be used for this purpose. The back sheet 7 generally defines the garment surface of the sanitary napkin. The back sheet 7 may be any means which is impervious to liquids and which prevents exudates absorbed and contained in the absorbent core 5 from soiling articles, such as panties, which come in contact with garment surface of the sanitary napkin 1. In the preferred embodiment of the sanitary napkin 1 illustrated in FIGS. 1 and 6, the back sheet 7 is a barrier sheet manufactured from a thin plastic film. Other flexible liquid impervious materials may also be used. Preferably, the back sheet 7 is a polyethylene film having a thickness of from about 0.012 millimeter to about 0.051 millimeter. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The back sheet 7 is preferably embossed and/or matte finished to provide a more clothlike appearance. Further, the back sheet 7 may permit vapours to escape from the absorbent core 5 which still preventing exudates from passing through the back sheet 7.

Preferably, the topsheet 3 and the back sheet 7 have length and width dimensions generally larger than the absorbent core 5 so that they extend beyond the longitudinal edges 9 and 11 of the absorbent core 5 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. In an embodiment, the back sheet 7 and the topsheet 3 have an elliptical shape and extend beyond the absorbent core 5 a distance of at least about 1.0 centimeter where they are joined directly to each other by attachment means as are well known in the art. The attachment means may be, for example, a uniform continuous layer of adhesive, patterned layer of adhesive, or an array of separate lines or spots of adhesive.

Figure 4:
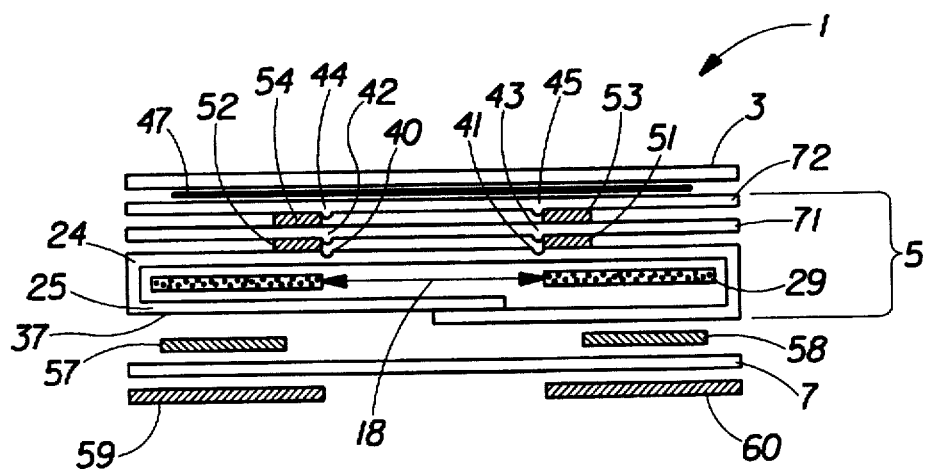
FIG. 4 shows a schematic cross sectional view of a preferred embodiment of sanitary napkin according to the invention along the transverse center line 16.

A preferred embodiment of a sanitary napkin has a cross-sectional configuration as shown in FIG. 4. The core 5 is straight-sided having a length of 210 mm and a width of 64 mm. The absorption layer (24, 25, 29) comprises an air laid tissue (24, 25) as supplied by Walkisoft, having a basis weight of 63 g/m$^{-2}$, wherein 6.5 g/square foot of absorbent gelling material of type L74 as supplied by Shokubai are comprised. Onto the absorption layer (24, 28, 29), a wipe acquisition sheet 71 being a hydroentangled nonwoven of a basis weight of 50.9 g/m$^2$, as supplied by Suominen, for lateral distribution of liquids across the layers 24, 25, is glued along the bond line 51, 52, using a spiral glue pattern. The bond lines 51, 52 have a length of 120 mm, a width of 5 mm, the distance W between the inner boundaries of the bond lines being 3 mm. The amount of glue used in each spiral glue pattern is 0.0075 gram, a distance between two adjacent loops in the spiral pattern being 5 mm. On top of the wipe acquisition sheet 71, a tissue 72 of generally lower density than the sheet 71 is located. The sheet 71 comprises an air laid tissue of basis weight 63 g/m$^2$ as supplied by Walkisoft. The sheet 72 is connected to the sheet 71 via glue lines 53 and 54, of similar type as glue lines 51, 52.

The glue used for affixing the sheet 71, 72 and 24 is a hot-melt adhesive of type Findley 990-374.

The topsheet 3 is fixed to the sheet 72 by means of a cold glue, type Findley 1-8082 which is applied as a film.

The score lines 40, 41, 42, 43, 44 and 45 are 120 mm in length, 1 mm wide and have a depth of 0.5 min. The distance between the score lines is 3 mm.

The garment facing surface 37 of the core 5 is glued to the backsheet 7 along two strips 57 and 58. The backsheet 7 is provided with a pressure sensitive glue along two strips 59 and 60. The parts of the garment facing surface 37 of the backsheet 7 that are located within a distance of 1.5 mm from the longitudinal center line 16 are free of adhesive.

Figure 5:
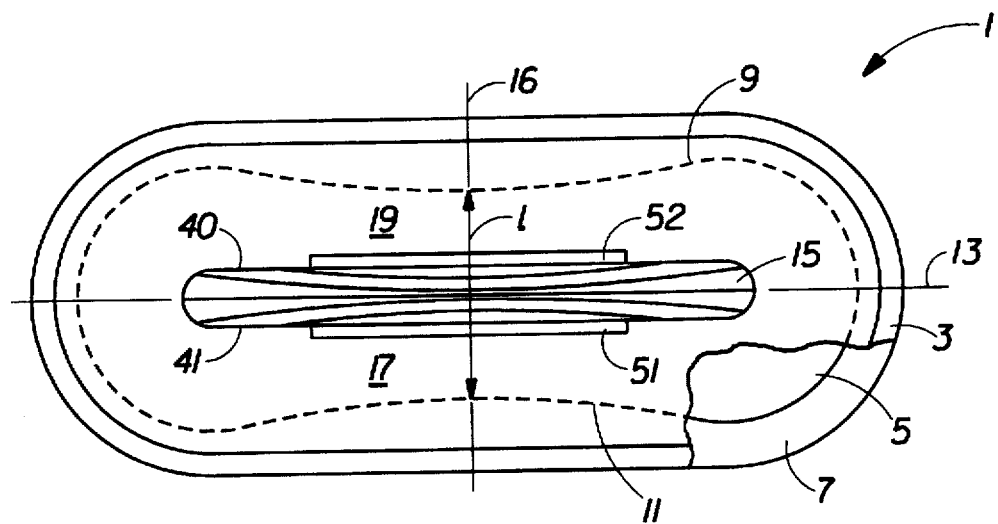
FIG. 5 shows a top plan view of a sanitary napkin having a central acquisition zone comprising embossments.

As shown in FIG. 5, the central acquisition zone 18, that is free of absorbent gelling material, is a closed contour, which is at all sides flanked by absorbent gelling material. The length of the central acquisition zone 18 is 147 mm, the width being 3 mm. Within the central pan 15 of the core, the central pan 15 comprising the central acquisition zone 18, the core 5 is provided with embossments for imparting extra flexibility to that zone.

Upon compression of the sanitary napkin along the sides 9, 11, the sanitary napkin of the construction as described above, assumes a generally W-shaped configuration as shown in FIGS. 6a and 6b, and relaxes back to its original shape when compressive forces are removed, thus maintaining good contact with the user's body and at the same time maintaining a sufficient coverage of the undergarment.

I claim:

1. A sanitary napkin for placement in a wearer's undergarment, comprising:
   - a liquid pervious topsheet;
   - a liquid impervious backsheet joined to said topsheet, said backsheet having a garment facing surface facing away from said topsheet; and
   - an absorbent core positioned between said topsheet and said backsheet, said absorbent core having a longitudinal centerline, a garment facing surface adjacent to said backsheet, a body facing surface being adjacent to said topsheet, and two axes of flexibility, one axis of flexibility extending on each side of the said longitudinal centerline and being substantially parallel thereto, said axes of flexibility defining a central part of said absorbent core wherein the stiffness of said absorbent core is reduced along the axes of flexibility, said garment facing surface of said core being joined to said backsheet along two strips of adhesive, said adhesive strips being spatially opposed and positioned on each side of said longitudinal centerline outwardly from said central part of said absorbent core,
   - a pair of adhesive strips for adhesively attaching said garment facing surface of said backsheet to a wearer's garment, said adhesive strips being spatially opposed and extending along and substantially outboard of said axes of flexibility.

* * * * *